United States Patent [19]

Church

[11] Patent Number: 4,623,351
[45] Date of Patent: Nov. 18, 1986

[54] ENDOPROSTHETIC BONE JOINT DEVICES

[75] Inventor: Jonathan C. M. Church, Bourne End, England

[73] Assignee: National Research Development Corporation, London, England

[21] Appl. No.: 601,929

[22] Filed: Apr. 19, 1984

[30] Foreign Application Priority Data

Apr. 20, 1983 [GB] United Kingdom ............... 8310675

[51] Int. Cl.[4] .............................................. A61F 2/32
[52] U.S. Cl. .................................................. 623/22
[58] Field of Search ................... 3/1.91, 1.912, 1.913; 128/92 C; 403/90, 4, 125, 135

[56] References Cited

U.S. PATENT DOCUMENTS

| | | | |
|---|---|---|---|
| 3,723,995 | 4/1973 | Baumann | 623/22 |
| 4,040,130 | 8/1977 | Laure | 128/92 C |
| 4,173,797 | 11/1979 | Langlais et al. | 623/22 |
| 4,206,517 | 6/1980 | Pappas et al. | 3/1.91 |
| 4,273,461 | 6/1981 | Kjellstrand et al. | 403/125 |
| 4,380,090 | 4/1983 | Ramos | 623/23 |

FOREIGN PATENT DOCUMENTS

| | | |
|---|---|---|
| 0066092A | 4/1982 | European Pat. Off. |
| 0051686A | 5/1982 | European Pat. Off. |
| 1292561 | 10/1972 | United Kingdom |
| 1414267 | 11/1975 | United Kingdom |
| 1416042 | 12/1975 | United Kingdom |
| 1548750 | 7/1979 | United Kingdom |
| 2029229A | 3/1980 | United Kingdom |
| 2117646 | 10/1983 | United Kingdom |

Primary Examiner—Richard J. Apley
Assistant Examiner—James Prizant
Attorney, Agent, or Firm—Cushman, Darby & Cushman

[57] ABSTRACT

An endoprosthetic acetabular component of overall cup form has three parts: an outer part (10) for securement in bone, an inner part (20) defining a dished articulation surface (23) and adjustably engageable with the outer part to allow independent variation of such surface in both inclination and rotation, and a third part (30) to secure the inner and outer parts with a preselected adjustment of the former. The inner/outer part engagement is preferably of spherical bearing form. Also, the inner part is preferably of two sub-parts (21, 24) respectively providing the articulation surface and the outer part engagement, the former sub-part being selectable from a range interchangeably connectable with the latter sub-part but having respectively different heights of articulation surface.

4 Claims, 1 Drawing Figure

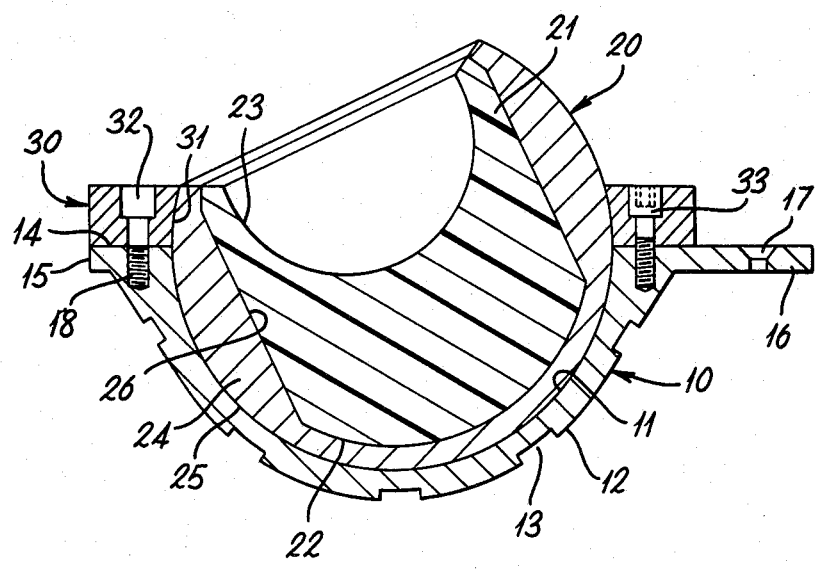

ENDOPROSTHETIC BONE JOINT DEVICES

This invention concerns endoprosthetic bone joint devices and more particularly such devices including a component of overall cup form to replace the acetabulum in the hip joint.

The invention in fact represents a further development of that described in UK Patent Specification No. 2117646A which latter provides an endoprosthetic acetabular component of overall cup form comprising an outer part and a plurality of inner parts individually selectively cooperable with said outer part, the outer part being adapted for securement to bone, and each inner part being interconnectable with said outer part in like manner and defining a dished articulation surface having a respectively different predetermined position relative to said outer part when connected therewith.

It is preferred that the inner parts of this last component afford a range of articulation surface positions which vary in depth and inclination relative to the outer part, and also that the outer and inner parts be rotatably adjustably interconnectable relative to the mouth of the overall cup form.

However, while such variations and adjustment capability are advantageous from a surgical point of view, the particular suggestions of said Specification for the practical provision of these features are thought to be open to improvement. For example, the variations in articulation surface position can require the provision of a considerable number of different inner parts and this is undesirable from the point of view of resultant cost. Also, the rotational adjustment capability involves complexity of shaping of the inner and outer part to allow indexed movement therebetween and, again, this is costly.

An object of the present invention is to improve this situation and, to this end, there is provided an endoprosthetic acetabular component of overall cup form comprising three parts of which the first is an outer part adapted for securement to bone, the second is an inner part defining a dished articulation surface and is adjustably engageable with said outer part to allow independent variation relative thereto of both the inclination and rotational position of said surface, and the third part is connectable with said outer part to secure said inner part in a preselected position of adjustment.

Preferably the engagement between the inner and outer parts involves the respective provision on such parts of convex and concave mutually complementary spherically-shaped surfaces interfaced to allow both of said variations. Clearly mechanical equivalents to such a spherical bearing arrangement are possible whereby the two variation capabilities are provided separately as it were, but those alternative arrangements will normally involve an increase in the necessary number of parts.

However, notwithstanding this last point, it is thought advatangeous for the inner part to comprise two sub-parts of which the innermost provides the articulation surface and the other provides a bearing surface affording positional variation. One benefit of this preference is that the sub-parts can be made from different materials best suited to the respective functional requirements. Also the provision of a replaceable innermost sub-part can simplify the provision of a range of parts affording different depths of articulation surface.

The third part of the proposed component is suitably of annular form connectable with the outer part as a locking ring to secure the inner part.

The invention and its preferred features as so far described may be clarified by consideration of the accompanying drawing which schematically illustrates one embodiment thereof in cross-sectional view.

The illustrated component has outer, inner and securement parts respectively denoted at 10, 20 and 30 in an assembly of overall cup form.

The outer part 11 is of cupped form having a hemispherically shaped interior surface 10 and a generally similar exterior surface 12 which is relieved by the provision of grooves 13 therearound. The rim 14 of the part is formed with a narrow radial flange 15 which is extended over part of its periphery into a lug 16 apertured at 17 for screw passage therethrough. The rim 14 is also formed with tapped bores 18 evenly distributed therearound.

The inner part 20 is of cupped form and comprised of two sub-parts also eahc of cupped form engaged one within the other. The innermost sub-part 21 is of circular cylindrical shape having one end surface 22 convexly spherically domed and a concave spherically dished surface 23 in its other end. The other sub-part 24 has a spherically shaped exterior surface 25 complementary with interior surface 11 of the outer part 10, but of greater than hemispherical extent. The interior surface 26 of sub-part 24 is complementary with the dome-end cylindrical shaping of the innermost sub-part 21.

The securement part 30 is an annular member having a radially interior surface 31 complementary with that portion of the exterior surface 25 of sub-part 24 which exceeds a hemisphere, and formed with axially-directed bores 32 in corresponding distribution with those 18 in the outer part 10.

Assembly of the component is evident from the drawing.

In use the component is to be deployed in general accordance with said Specification No. 2117646A. This involves first securing the outer part 10 in a suitably prepared acetabular cavity, then determining an optimal location for the surface 23 as a prosthetic acetabulum with the inner part 20 adjustably seated in the outer part to form a spherical bearing, and finally securing the inner part in the desired location in the outer part by screw connection as at 33 of the part 30 as shown to the outer part.

While the invention has been described with more particular reference to the illustrated embodiment, this is by way of example only and variation of detail is clearly possible within the more general discussion of the invention given first above.

For example the outer part 10 is seen to be suited to securement by use of bone cement and/or screws by virtue of its ribbed outer surface and apertured lug, but other securement techniques can be deployed.

Similarly, the parts are indicated by their cross-sectioning to be made of metal, except for the innermost sub-part 21 which is of plastics material, but other materials can be used. The indicated choice of materials follows the common usage of plastics material to afford low friction engagement in articulation at the surface 23, while at the same time, by virtue of the present invention, the plastics sub-part can be wholly backed by metal and the seating in the bone can be of metal to afford mechanical stability.

This last benefit follows in part from the formation of the inner part 20 from two sub-parts and this additionally facilitates the provision of a choice of articulation surface depth by way of a range of innermost sub-parts of simple form and relatively low cost material. Moreover, a simple snap-fit connection between the sub-parts can be used as indicated by the slight necking in the region of their mouths. However, other arrangements are possible including the use of a one-piece inner part.

Yet further variations are clearly possible and some of these, such as the provision of a range of outer parts to afford a choice of bone-securement techniques and the use of an ovalate exterior surface for the outer part, will be evident from said Specification No. 2117646A.

I claim:

1. An acetabular component of an endoprosthesis, said component being of overall cup form and comprising:
   a first outer part adapted for securement to bone;
   a second inner part defining a dished articulation surface and adjustably engaged in said outer part to allow independent variation relative thereto of both the inclination and the rotational position of said surface while exposing such surface; and
   a third part engaged with said inner part separately from said surface to maintain the exposure thereof and separately connected with said part to secure said inner part in a preselected fixed position of adjustment.

2. A component according to claim 1 wherein said inner and outer parts respectively define convex and concave surfaces of complementary spherical shape mutually engaged as a spherical bearing assembly.

3. A component according to claim 1 wherein said inner part comprises two sub-parts engageable one within the other, the inner sub-part providing said articulation surface and the outer sub-part providing a bearing surface affording positional variation in said outer part.

4. A component according to claim 1 wherein said third part is of annular form connectable with said outer part as a locking ring to secure said inner part therein.

* * * * *